(12) United States Patent
Vaddadi

(10) Patent No.: US 6,919,330 B2
(45) Date of Patent: Jul. 19, 2005

(54) FORMULATIONS OF DRUGS

(75) Inventor: Krishnarao Sitaramrao Vaddadi, Melbourne (AU)

(73) Assignee: Laxdale Limited, Stirling (GB)

( * ) Notice: Subject to any disclaimer, the term of this patent is extended or adjusted under 35 U.S.C. 154(b) by 0 days.

(21) Appl. No.: 10/359,552

(22) Filed: Feb. 7, 2003

(65) Prior Publication Data

US 2003/0175361 A1 Sep. 18, 2003

(30) Foreign Application Priority Data

Feb. 7, 2002 (GB) ............................................. 0202900

(51) Int. Cl.$^7$ ........................ A61K 31/55; A61K 33/04; A01N 59/02
(52) U.S. Cl. ...................................... 514/220; 424/702
(58) Field of Search ........................... 514/220; 424/702

(56) References Cited

U.S. PATENT DOCUMENTS

| | | | | |
|---|---|---|---|---|
| 4,310,952 A | * | 1/1982 | Robben et al. | 424/244 |
| 5,358,720 A | | 10/1994 | Koppel et al. | 424/639 |
| 5,760,037 A | * | 6/1998 | Galey et al. | 514/245 |
| 6,077,828 A | | 6/2000 | Abbruzzese et al. | 514/21 |
| 6,090,414 A | * | 7/2000 | Passwater et al. | 424/702 |
| 2002/0001575 A1 | | 1/2002 | Foremann | 424/93 |

FOREIGN PATENT DOCUMENTS

| | | |
|---|---|---|
| EP | 0345247 A2 | 12/1989 |
| EP | 1163904 | 12/2001 |
| GB | 2280110 | 1/1995 |
| WO | WO-9528937 | * 11/1995 |
| WO | WO95/28937 | 11/1995 |
| WO | WO-9848788 | * 11/1998 |

OTHER PUBLICATIONS

Loncar–Stevanovic et al, Jour of Envir Path, Tox & Onc, vol. 17, No. 3–4, 1998, pp. 331–337, The influence of selenium and . . .

Kurihara et al, No to Hattatsu, vol. 32, No. 4, Jul. 2000, pp. 346–351, Two Sibling Patients with Non–Fukuyama Type . . .

Fryer, The Lancet, vol. 354, No. 9186, Oct. 9, 1999, pp. 1300–1301, Antioxidants and Friedreich's Ataxia.

Yung, Pharmacology Bioc & Behavior, vol. 21, Suppl. 1, 1984, pp. 41–47, Synopsis on Metals in Medicine and Psychiatry.

Kilian et al, LANCET, vol. 354, Nov. 27, 1999, pp. 1841–1845, Myocarditis and cardiomyopathy associated with clozapine.

La Grenade et al, N Engl J Med, vol. 345, No 3, Jul. 19, 2001, pp. 219–225, Recombinant Human Activated Protein C for . . .

Linday et al, J Clin Psychopharmacol, vol. 15, No 5, pp. 353–359 Free Radical Scavenging Enzyme Activity and Related Trace . . .

Rayman, LANCET, vol. 356, Jul 15, 2000, pp. 233–241, The importance of selenium to human health.

Beck et al, Nature Medicine, vol. 1, Nov. 1995, pp. 433–436, Rapid genomic evolution of a non–virulent Coxsackievirus . . .

* cited by examiner

*Primary Examiner*—Alton Pryor
(74) *Attorney, Agent, or Firm*—Jacobson Holman PLLC

(57) ABSTRACT

The treatment of psychiatric or neurological disorders using selenium in combination with drugs used conventionally to treat such disorders is disclosed. The daily dose of selenium is between 10 μg and 2000 μg per day.

8 Claims, No Drawings

FORMULATIONS OF DRUGS

Risk of cardiovascular illness is very common in patients who are also being treated for psychiatric and neurological disorders. It is uncertain whether this is due to the underlying illness or whether it is due to the drugs which are used to treat that illness but many commentators have pointed out that the drugs themselves may precipitate cardiac arrhythmias, myocarditis and cardiomyopathies. The information for doctors about drugs, particularly but not only ones for psychiatric and neurological disorders, authorised by regulatory authorities such as the United States Food and Drug Administration (FDA) frequently contain warnings about possible cardiovascular side effects. Clozapine is one drug which carries a high risk (G J Killian et al, Lancet 1999; 354: 1841–5. L La Grenade et al, N Engl J Med 2001; 345: 224–5). Clozapine can also cause depression of white cell counts and in the worst cases complete loss of normal white blood cell production (agranulocytosis).

The present invention relates to the co-administration of selenium together with a drug for the treatment or prevention of psychiatric or neurological disorders and particularly with clozapine. The invention provides pharmaceutical formulations comprising a drug for the treatment or prevention of psychiatric or neurological disorders together with any biologically assimilable form of selenium, such that when the drug is administered the daily dose of selenium is between 10 µg and 2000 µg per day.

Preferably, the daily dose of selenium provided by the formulations of the present invention is between 50 µg and 500 µg/day and very preferably between 150 and 300 µg/day.

The selenium may be provided in the form of selenium yeast, selenomethionine, selenocysteine or any appropriate selenite or selenate compound. This may form a component of the formulation. Alternatively the selenium may be chemically linked to the drug to form a selenium-drug derivative.

The drug of the formulations of the present invention is one used for the prevention or treatment of psychiatric or neurological disorders. The drug may be one approved by a regulatory authority for such a treatment, including the US Food and Drug Administration (FDA) or the European Medicines Evaluation Agency (EMEA). The preferred invention is not to combine selenium with other multivitamin preparations, which have not been approved for administration to patients with psychiatric or neurological disorders. Preferably, the drug is one used for the treatment or prevention of psychiatric disorders including schizophrenia and bipolar disorder. The drug clozapine is particularly suited for the formulations of the present invention.

The formulations are preferably orally administrable.

In a second aspect of the invention, the selenium and the drug may be formulated separately but provided in the same pack with instructions for co-administration. The present invention provides a pack containing the selenium and the drug packaged for co-administration.

In a third aspect of the invention there is provided a method for the treatment or prevention of any neurological or psychiatric disease by the co-administration of a drug conventionally used to treat that disease together with selenium in any biologically assimilable form in a daily dose of between 10 µg and 2000 µg selenium per day. The treatment may be by separate administration of the drug and the selenium, or by administration of a formulation of the first aspect of the invention.

The invention further provides use of a formulation of the first aspect of the invention in the manufacture of a medicament for the treatment or prevention of any neurological or psychiatric disease.

The treatments are of psychiatric or neurological disorders. Preferably, the invention is used to treat psychiatric disorders including but not limited to schizophrenia, bipolar disorder, depression, anxiety disorders and personality disorders. Alternatively, the invention is for the treatment or prevention of neurological disorders including but not limited to epilepsies, Parkinson's disease, dementias of both Alzheimer and vascular types, Huntington's disease, spinocerebellar ataxias, Friedreich's ataxia, myotonic dystrophy, amyotrophic lateral sclerosis and multiple sclerosis.

The present invention also provides a method for the reduction of side effects caused by administration of a drug for the treatment of a psychiatric or neurological disorder to a patient by the co-administration, separately or in a formulation according to the first aspect of the invention, of the drug together with selenium in any biologically assimilable form to provide a daily dose of between 10 µg and 2000 µg selenium per day.

In most cases it is likely that the preferred range of selenium to used will be in the range of 50 to 500 µg/day and very preferably in the range of 150 to 300 µg/day.

The present invention is described in particular with reference to the treatment of cardiovascular illness in patients who are also being treated for psychiatric and neurological disorders. The cause of the risk of developing this illness is unknown and multiple factors may be involved. One pilot study has reported that schizophrenic patients on clozapine, a drug conventionally used to treat schizophrenia, have low selenium levels (L A Linday et al, J Clin Psychopharmacol 1995; 15: 353–60). This looked at only a few patients, however, did not analyse selenium in schizophrenic patients on other drugs, and did not look at selenium levels in patients with other disorders.

For the present invention, a large study has been carried out in normal individuals, in patients with various mood disorders including depression and bipolar disorder, in schizophrenic patients on drugs other than clozapine, and in schizophrenic patients on clozapine. The results are shown in Table 1 below. Here the selenium levels are expressed in µmol/litre and are shown as means plus or minus the Standard Error of the Mean (SEM)

TABLE 1

|  | Healthy controls | Mood disorders | Schizophrenia clozapine | Schizophrenia other drugs |
| --- | --- | --- | --- | --- |
| N | 56 | 36 | 57 | 42 |
| Mean age | 43.1 | 40.6 | 36.1 | 37.3 |
| Plasma Se | 1.49 ± 0.04 | 1.39 ± 0.05 | 1.28 ± 0.04 | 1.47 ± 0.06 |
| Red cell Se | 1.80 ± 0.08 | 1.70 ± 0.07 | 1.47 ± 0.07 | 1.70 ± 0.07 |

This shows that all of the groups of patients, irrespective of what drugs they were on, exhibited low selenium levels, but that the levels were exceptionally low in the schizophrenic patients on clozapine.

Selenium is a constituent of many enzymes, particularly ones involved in antioxidant defences (MP Rayman, Lancet 2000; 232–240). Selenium deficiency leads to a particular risk of cardiovascular disease, especially myocarditis and cardiomyopathy. Selenium deficiency also increases susceptibility to the serious cardiac complications of viral infections (M A Beck et al, Nature Medicine 1995; 1: 433–6).

The present invention is based on the inventor's suggestion that selenium deficiency is a major cause of the cardiovascular and perhaps other problems which are associated with the ingestion of drugs for psychiatric and neurological disorders, and especially clozapine where selenium will also be helpful in preventing the depression of white cell counts and agranulocytosis.

In order to reduce the risks of drug administration, it is now proposed that all drugs for neurological and psychiatric disorders should be formulated with sufficient selenium to prevent and correct any selenium deficiency. Though it is not clear why drugs so commonly are associated with selenium deficiency, it is now suggested that some of them increase selenium excretion or impair selenium absorption into the body. It may therefore be necessary to incorporate levels of selenium into the drug formulation to provide a daily intake of selenium either around the normal daily requirement of selenium or, in appropriate cases, daily intakes several times higher than that.

Various official bodies have made recommendations about the usual daily selenium requirement (M Rayman 2000, Lancet 356: 233–241). These range from a low of about 50 μg/day to a high of around 100 μg/day. However, these figures do not take into account the possibility that drugs or illnesses may interfere with selenium absorption or excretion and the present invention therefore proposes that the broad range of selenium supplementation needed by those taking therapeutic drugs may range from a low of 10 μg/day in those whose selenium intakes are adequate or near adequate to a high of 2000 μg/day in those who have particular problems with selenium metabolism or absorption. In most cases it is likely that the preferred range of supplemental selenium to be added to the drug will be in the range of 50 to 500 μg/day and very preferably in the range of 150 to 300 μg/day.

This is illustrated by a further experimental study on giving selenium to patients with schizophrenia who were taking clozapine or other psychiatric drugs (see table 2)

TABLE 2

SELENIUM TREATMENT

| | Age | Length of Illness | Diagnosis | Date | Plasma Se | RBC Se | SELENIUM GIVEN | MEDICATION |
|---|---|---|---|---|---|---|---|---|
| Male | 25 | Since 1998 | Schizophrenia | Feb. 09, 2002<br>Jul. 10, 2002 | 1.2<br>2.1 | 1.4<br>1.9 | Feb. 09, 2002<br>(200 mcg) | Clozapine<br>450 mg nocte |
| Female | 26 | Since 1992 | Schizophrenia | Feb. 09, 2002<br>Jul. 10, 2002 | 1.2<br>2.3 | 1.9<br>2.4 | Dec. 09, 2002<br>(200 mcg) | Epilim 1000/d;<br>4 mg/d;<br>Zoloft 200 mg/d;<br>Marine 3 g/d;<br>Vitamin B |
| Female | 22 | 2 years + | Schizophrenia | Feb. 09, 2002<br>Jul. 10, 2002 | 1.2<br>2.2 | 1.5<br>2.0 | Feb. 09, 2002<br>(200 mcg) | Clozapine<br>600 mg/d;<br>Epilim<br>2000 mg/d;<br>Logynon ED 1/d |
| Male | 41 | 25 years | Schizophrenia<br>Mild Autism | Feb. 09, 2002<br>Jul. 10, 2002 | 1.1<br>2.3 | 1.3<br>2.1 | Feb. 09, 2002<br>(200 mcg) | Clozapine<br>800 mg/d;<br>Losec 20 mg/d;<br>Clonazepam<br>3 mg/d;<br>Benzotropine<br>4 mg/d; +<br>laxatives |
| Female | 22 | 3 years | Schizophrenia | Mar. 06, 2002<br>Jul. 06, 2002<br>Nov. 07, 2002 | 1.3<br>1.0<br>1.2 | 1.0<br>1.0<br>1.3 | May 06, 2002<br>(100 mcg) | Risperidone<br>8 mg/d; Levlen<br>ED 1/d;<br>Quetiapine<br>400 mg/d;<br>Vitamin E<br>1 g/d;<br>FGF Iron 1/d |
| Male | 22 | 4 years | Schizophrenia | Feb. 09, 2002<br>14/10/02 | 0.8<br>1.9 | 1.3<br>1.9 | 19/09/02<br>(200 mcg) | Clozapine<br>300 mg/d;<br>Epilim<br>1500 mg/d<br>Stelazine<br>5 mg/d; Maxepa<br>4 g/d;<br>Ranitidine<br>300 mg/d;<br>Benzhexol<br>5 mg/d;<br>Maxalon<br>20 mg/d;<br>Lithium<br>500 mg/d |
| Male | 28 | Since May 2001 | Schizophrenia | Feb. 09, 2002<br>Jul. 10, 2002 | 1.5<br>2.1 | 2.4<br>2.8 | Feb. 09, 2002<br>(200 mcg) | Clozapine<br>300 mg nocte |

TABLE 2-continued

SELENIUM TREATMENT

|  | Age | Length of Illness | Diagnosis | Date | Plasma Se | RBC Se | SELENIUM GIVEN | MEDICATION |
|---|---|---|---|---|---|---|---|---|
| Female | 37 | 8 years | Schizophrenia | Feb. 09, 2002<br>Jul. 10, 2002 | 1.1<br>2.5 | 1.5<br>2.4 | Feb. 09, 2002<br>(200 mcg) | Clozapine 400 mg/d; Citalopram 60; Zuclopenthixol 300 mg I.M. 2/52; Temazepam 10 mg/d; Lithium 900 mg/d; Benzotropine 2 mg/d |
| Male | 38 | 12 years | Schizophrenia | Feb. 09, 2002<br>Jul. 10, 2002 | 1.2<br>2.4 | 1.6<br>2.3 | Feb. 09, 2002<br>(200 mcg) | Clozapine 700 mg/d; Epilim 2 g/d |

Nine patients were studied. Prior to treatment all patients had red cell and plasma selenium levels in the lower part of the range for psychiatric patients. Eight of the patients were given 200 µg of selenium per day in the form of selenium yeast and one was given 100 µg per day. At the end of the supplementation period, all the eight patients who were given 200 µg per day showed plasma and red cell selenium levels in the upper part of the range for normal individuals. However, the patient given 100 µg per day showed no change in plasma selenium and only a small rise in red cell selenium. This indicates that for many patients 100 µg per day is unlikely to be sufficient whereas 200 µg per day is likely to be sufficient giving rise to a preferred range of daily doses from 150 µg to 300 µg per day.

The selenium may be provided in any form which may be assimilated by the body. Many selenium supplements are prepared by growing yeast or possibly other micro-organisms on selenium-containing medium and such yeast or other micro-organism derived sources would be appropriate. Selenium may also be chelated or otherwise linked to a range of other compounds, and in particular amino acids. Selenomethionine and selenocysteine are common naturally occurring compounds which are widely used as selenium supplements. Inorganic salts of selenite and also selenate may be used. Any assimilable form of selenium may be employed.

The selenium may be incorporated into the actual drug delivery system whether that be tablets, liquids or emulsions, hard or soft gelatin capsules, powders, drinks, foods or any other appropriate system which may be used by those skilled in the art to deliver either a drug or a selenium product. Usually the selenium will actually be incorporated into the drug formulation or may be chemically linked to the drug to form a selenium-drug derivative. Sometimes it may be appropriate to provide the selenium in a separate formulation but linked to the drug in a combination package.

EXAMPLE FORMULATIONS

1. A tablet formulation of any drug for a neurological or psychiaric disorder formulated together with a selenium compound which delivers a daily amount of selenium between 10 µg and 2000 µg. The selenium may be in any biologically assimilable form including yeast selenium, selenomethionine, selenocysteine, sodium selenite or sodium selenate.

2. As in example 1 where the formulation is a hard or soft gelatin capsule.

3. As in example 1 where the formulation is a liquid or an emulsion with or without flavouring.

4. As in example 1 where the formulation is in any other form appropriate for oral administration including a powder or a liquid.

5. As in examples 1–4 where the drug is clozapine or one of its derivatives.

6. As in examples 1–4 where the drug is any drug for the treatment of schizophrenia including but not limited to chlorpromazine, haloperidol, risperidone, olanzapine, quetiapine, zotepine, amisulpiride, ziprasidone, sertindole, ethyl eicosapentaenoate or aripiprazole.

7. As in examples 1–4 where the drug is any drug for the treatment of depression including but not limited to amitriptyline, lofepramine, dothiepin, doxepin, trimipramine, imipramine, clomipramine, protriptyline., nortriptyline, venlafaxine, fluoxetine, fluvoxamine, sertraline, paroxetine, citalopram, escitalopram, reboxetine, mirtazepine, nefazodone, trazodone, moclobemide, viloxazine, maprotiline, phenelzine, tranylcypromine or ethyl-eicosapentaenoate.

8. As in examples 1–4 where the drug is any drug for the treatment of bipolar disorder, including but not limited to lithium salts, valproic acid and its derivatives and carbamazepine.

9. As in examples 1–4 where the drug is any drug for the treatment of anxiety including but not limited to any benzodiazepines, any beta-blockers and buspirone.

10. As in examples 1–4 where the drug is any drug for the treatment of epilepsy including but not limited to carbamazepine, lamotrigine, sodium valproate, phenytoin, benzodiazepines, barbiturates, topiramate, gabapentin or vigabatrin.

11. As in examples 1–4 where the drug is any drug for the treatment of Parkinson's disease including but not limited to levodopa, benserazide, carbidopa, selegiline, tolcapone, bromocriptine, ropinirole, apomorphine, pergolide, other dopamine receptor agonists, amantadine or anticholinergic drugs.

12. As in examples 1–4 where the drug is any drug for the treatment of Huntington's disease, Friedreich's ataxia, myotonic dystrophy, amyotrophic lateral sclerosis., multiple sclerosis or any other neurodegenerative disease including but not limited to ethyl-eicosapentaenoate, riluzole, lofepramine and cyclo-oxygenase 2 inhibitors.

13. As in examples 1–4 where the drug is any drug for the treatment of any form of dementia including but not limited to donepezil, rivastigmine, or galantamine or any cholergic drug.

What is claimed is:

1. A method of treating schizophrenia in a subject by adding to clozapine used to treat the schizophrenia any biologically assimilable form of selenium such that when the clozapine is administered to said subject the daily dose of selenium is between 10 μg and 2000 μg per day.

2. The method according to claim 1, wherein the daily dose of selenium is between 50 μg and 500 μg per day.

3. The method according to claim 1, wherein the daily dose of selenium is between 150 μg and 300 μg per day.

4. The method according to claim 1, wherein the selenium is in the form of selenium yeast.

5. A method of treating schizophrenia in a subject by the co-administration to said subject of clozapine together with selenium in any biologically assimilable form in a daily dose of selenium is between 10 μg and 2000 μg per day.

6. The method according to claim 5, wherein the daily dose of selenium is between 50 μg and 500 μg per day.

7. The method according to claim 6, wherein the daily dose of selenium is between 150 μg and 300 μg per day.

8. The method according to claim 5, wherein the selenium is in the form of selenium yeast.

* * * * *